US00PP27181P3

(12) United States Plant Patent
Danziger

(10) Patent No.: US PP27,181 P3
(45) Date of Patent: Sep. 20, 2016

(54) ***COREOPSIS* PLANT NAMED 'DCOREO202'**

(50) Latin Name: *Coreopsis cordata*
Varietal Denomination: DCOREO202

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 140 days.

(21) Appl. No.: 13/999,983

(22) Filed: Apr. 11, 2014

(65) Prior Publication Data

US 2015/0296678 P1 Oct. 15, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Keith Robinson
(74) *Attorney, Agent, or Firm* — Cassandra Bright

(57) ABSTRACT

A new and distinct *Coreopsis* cultivar named 'DCOREO202' is disclosed, characterized by long, continuous flowering on highly floriferous plants. Large flowers of intense color, mounded plant habit and good branching creating a dense and full body. The new variety is a *Coreopsis*, normally produced as an outdoor garden or container plant.

2 Drawing Sheets

Figure 1:
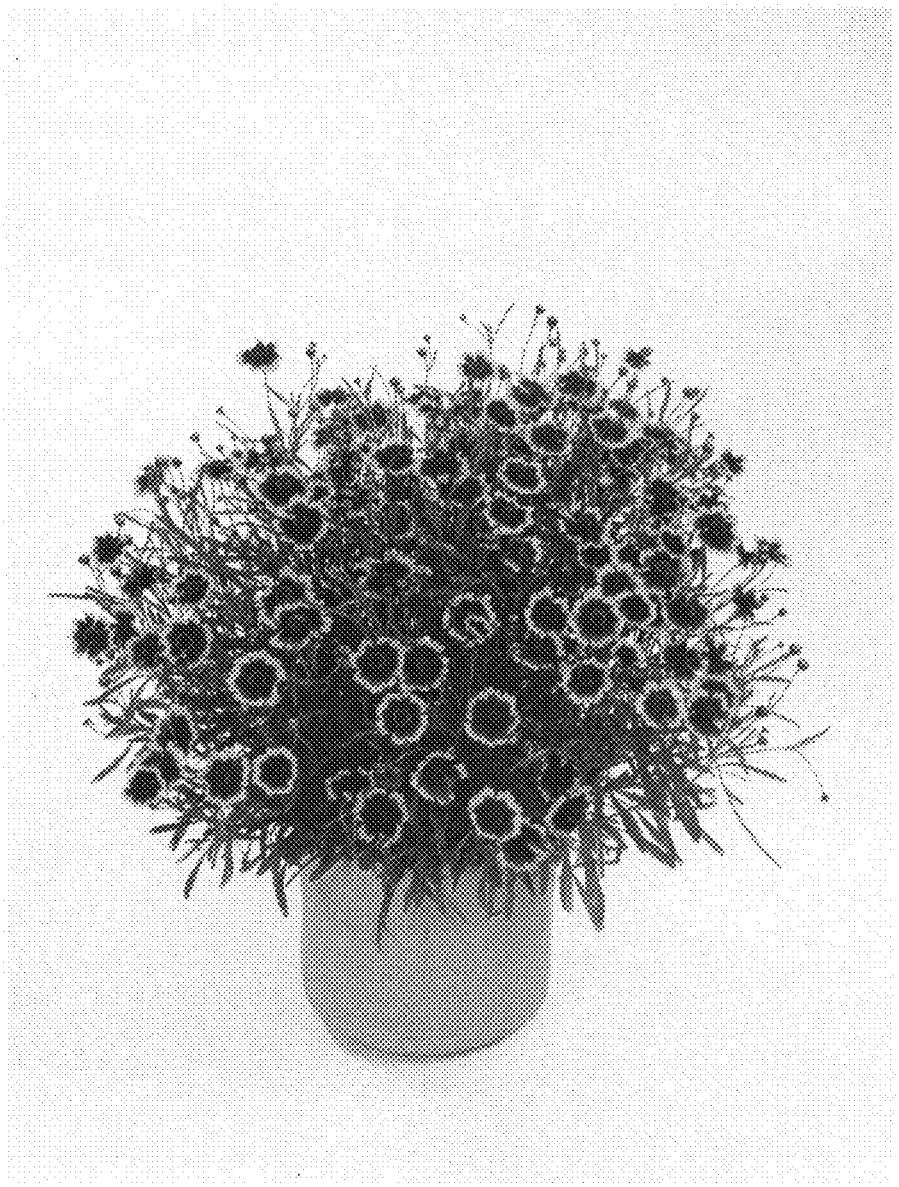

Latin name of the genus and species: *Coreopsis cordata.*
Variety denomination: 'DCOREO202'.

BACKGROUND OF THE INVENTION

The new *Coreopsis* cultivar is a product of a planned breeding program conducted by the inventor, Gavriel Danziger, in Moshav Mishmar Hashiva, Israel. The objective of the breeding program was to produce new *Coreopsis* varieties for ornamental commercial applications. The open pollination resulting in this new variety was made during June of 2010.

The seed parent is the unpatented, proprietary seedling variety referred to as *Coreopsis cordata* 'co-z-41' The pollen parent is unknown as it was an open pollination breeding program. The new variety was discovered in July of 2011 by the inventor in a group of seedlings resulting from the 2010 open pollination, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel during December of 2010 and has shown that the unique features of this cultivar are stable and reproduced true to type in more than 30 successive generations.

SUMMARY OF THE INVENTION

The cultivar 'DCOREO202' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCOREO202' These characteristics in combination distinguish 'DCOREO202' as a new and distinct *Coreopsis* cultivar:

1. Good branching—dense and full bodied plant.
2. Large flowers with intense color.
3. Long & continuous flowering period.
4. Mounded habit.
5. Highly floriferous—many flowers are fully open at the same time.

Plants of the new cultivar 'DCOREO202' are similar to plants of the seed parent, *Coreopsis cordata* 'co-z-41' in most horticultural characteristics, however, plants of the new cultivar 'DCOREO202' differs in the following:

1. Fuller and denser plant structure.
2. More abundant flowering.
3. Shorter in height.

COMMERCIAL COMPARISON

Plants of the new cultivar 'DCOREO202' are comparable to the commercial variety *Coreopsis* 'Limbo' U.S. Plant Pat. No. 22,130. The two *Coreopsis* varieties are similar in most horticultural characteristics; however, the new variety 'DCOREO202' differs in the following:

1. Fuller and denser plant structure.
2. More abundant flowering.
3. Wider leaf.
4. 'DCOREO202' has bi-color red and yellow flowers compared to creamy white flowers of 'Limbo'.
5. Shorter in height.

Plants of the new cultivar 'DCOREO202' are also comparable to the commercial variety *Coreopsis* 'Mambo' U.S. Plant Pat. No. 22,131. The two *Coreopsis* varieties are similar in most horticultural characteristics; however, the new variety 'DCOREO202' differs in the following ways:

1. Fuller and denser plant structure.
2. More abundance flowering.
3 'DCOREO202' has bi-color red and yellow flowers compared to bi-color dark pink and light pink flowers of 'Mambo'.
4. Shorter in height

BRIEF DESCRIPTION OF THE PHOTOGRAPHS

The accompanying photograph in FIG. 1 illustrates in full color a typical plant of 'DCOREO202' grown in a greenhouse, in a 12 cm pot. Age of the plant photographed is approximately 12 weeks from planting.

Figure 2:
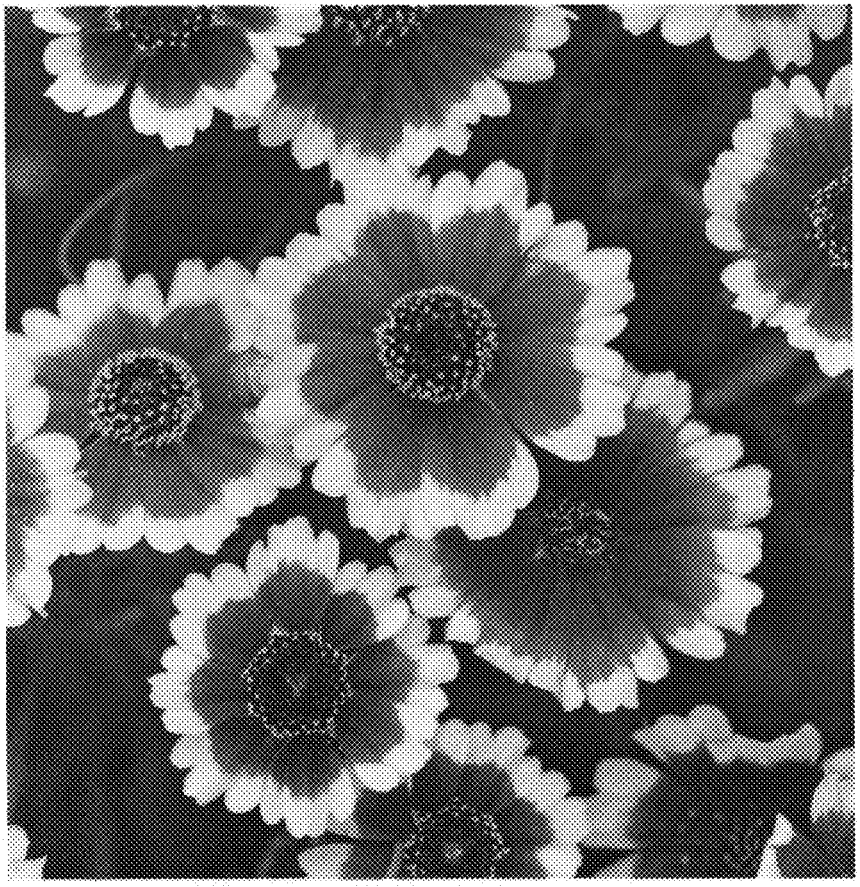

FIG. 2 illustrates a close up of the flowers.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DCOREO202' plants grown in a nursery during Fall of 2013 in Moshav Mishmar Hashiva, Israel. The growing temperature ranged from 18° C. to 28° C. during the day and from 10° C. to 12° C. during the night. Measurements and numerical values represent averages of typical plant types.

Botanical classification: *Coreopsis cordata* 'DCOREO202'.

PROPAGATION

Typical propagation material: Cuttings.
Time to rooting.: 10 days at approximately 25° C.
Root description: Fine, fibrous roots.

PLANT

Age of plant described: Approximately 70 days old.
Pot size of plant described: 12 cm.
Growth habit: Mounded.
Height: Approximately 20-25 cm.
Plant spread: Approximately 30 cm.
Growth rate: Moderate.
Branching characteristics: Well branched.
Length of lateral branches: Approximately 18-20 cm.
Diameter of lateral branches: Approximately 2.5-3 cm.
Texture of lateral branches: Smooth, glossy.
Internode length: Approximately 3 cm.
Strength of stem: Flexible, not easily broken.
Color of lateral branches: Near yellow-green group 146C RHS.
Aspect/angle of branches: 45 degrees upwards from primary branch.
Number of leaves per lateral branch: Approximately 15-20.

FOLIAGE

Leaf:
- *Arrangement*.—Opposite.
- *Average length*.—Approximately 5 cm.
- *Average width*.—Approximately 0.5-0.8 cm.
- *Shape of blade*.—Oblanceolate (inversely lance-shaped).
- *Apex*.—Obtuse.
- *Base*.—Pointed, acute.
- *Margin*.—Entire.
- *Texture of top surface*.—Smooth.
- *Texture of bottom surface*.—Smooth.
- *Appearance top surface*.—Matte.
- *Appearance bottom surface*.—Matte.
- *Color*.—Young foliage upper side: Near yellow-green group 144A RHS. Young foliage under side: Near yellow-green group 146B RHS. Mature foliage upper side: Near green group 137C RHS. Mature foliage under side: Near yellow-green group 146B RHS.

Venation:
- *Type*.—Pinnate.
- *Venation color upper side*.—Near yellow-green group 146B RHS.
- *Venation color under side*.—Near yellow-green group 144A RHS.

Petiole:
- *Petiole*.—Present.
- *Length*.—1.5 cm.
- *Strength*.—Very flexible, strong.
- *Diameter*.—0.1 cm.
- *Pubescence*.—Absent.
- *Color*.—Near yellow-green group 146C RHS.

FLOWER

Bloom period: From early Spring (March) to late Fall (October) under moderate weather such as in Israel.

Bud:
- *Bud shape*.—Globular.
- *Bud length*.—Approximately 0.5 cm.
- *Bud diameter*.—Approximately 0.4 cm.
- *Bud color*.—Near yellow-green group 152A RHS.

Inflorescence: Singly occurring composite flowers.

Flower:
- *Diameter of entire flower*.—Approximately 3 cm.
- *Depth of flower*.—Approximately 0.8 cm.
- *Diameter of disc*.—Approximately 0.7 cm.
- *Depth of disc*.—Approximately 0.4 cm.

Ray florets:
- *Number of ray florets*.—8 Avg.
- *Length*.—Approximately 1.4 cm.
- *Width*.—Approximately 1.0 cm.
- *Shape*.—Obcordate, but, typically with more than 2 lobes.
- *Apex shape*.—Irregular rounded lobes.
- *Margin*.—Wavy.

Color:
- *Ray florets*.—Upper surface at first opening: Near yellow-orange group 17A RHS at Tip, and near greyed-purple group 187A near disk. Upper surface at maturity: Near yellow-orange group 17A RHS at Tip, and near greyed-purple group 187B near disk. Upper surface at fading: Near yellow-orange group 17A RHS at Tip, and near greyed-purple group N186C RHS near disk. Under surface at first opening: Near yellow group 13A RHS at Tip, and near greyed-orange group 177A near disk. Under surface at maturity: Near yellow-orange group 17B RHS at Tip, and near greyed-purple group 178A near disk. Under surface at fading: Near yellow-orange group 21A RHS at Tip, and near Brown group 200B near disk.
- *Disc florets*.—Number of Disc Florets: Average 60. Length: Approximately 2.5 cm. Width: Approximately 0.05 cm. Shape: Oblong. Margin: Entire. At first opening: Near greyed-purple 187A RHS. At maturity: Near greyed-purple 187A RHS. At fading: Near greyed-purple N186A RHS.

Fragrance: Faint.

Phyllaries/involucral bracts:

*Number*.—Approximately 8.

*Sepal length*.—Approximately 0.5 cm.

*Sepal width*.—Approximately 0.2 cm.

*Sepal texture*.—Smooth, stiff.

*Apex shape*.—Acute.

*Margin*.—Entire.

*Color*.—Transparent, near yellow-orange group 17A RHS.

Peduncle:

*Peduncle length*.—Approximately 6-8 cm.

*Peduncle diameter*.—Approximately 0.2 cm.

*Angle*.—Not relevant as it is a whole flower.

*Color*.—Near yellow-green 144A RHS.

*Peduncle texture*.—Smooth, slightly glossy.

*Peduncle strength*.—Medium.

REPRODUCTIVE ORGANS

Disc florets:

*Androecium*.—Present.

*Stamens*.—2 fused lobes.

*Anther shape*.—Rounded.

*Anther length*.—Approximately 0.1 cm.

*Anther color*.—Near grayed-purple 187A RHS.

*Pollen quantity*.—Moderate.

*Pollen color*.—Near RHS Yellow 7B.

Gynoecium:

*Pistil number*.—One per disc floret.

*Pistil shape*.—Oblong, trumpet shaped.

*Pistil length*.—Approx. 0.6 cm.

*Style length*.—Approx. 0.4 cm.

*Style color*.—Near green-yellow 1B RHS.

*Stigma shape*.—Cleft.

*Stigma color*.—Near red 46B RHS.

*Ovary diameter*.—0.07.

*Ovary color*.—Near green-yellow 1B RHS. Reproductive organs not typically found in ray florets.

OTHER CHARACTERISTICS

Disease/pest resistance: Neither resistance nor susceptibility to normal diseases and pests of *Coreopsis* have been observed.

Drought tolerance and cold tolerance: Tolerant of hot, humid summer climates.

Fruit/seed production: Seeds observed.

Seed:

*Shape*.—Oblong with cleft tip.

*Color*.—Near brown group 200A RHS.

*Size*.—Approximately 0.5 cm in length and 0.1 cm in width.

What is claimed is:

1. A new and distinct cultivar of *Coreopsis* plant named 'DCOREO202' as herein illustrated and described.

* * * * *